United States Patent [19]
Penick

[11] Patent Number: 5,639,930
[45] Date of Patent: Jun. 17, 1997

[54] PROCESS OF PRODUCING ALKYLATES

[76] Inventor: Joe E. Penick, 181 Library Pl., Princeton, N.J. 08540

[21] Appl. No.: 368,533

[22] Filed: Jan. 4, 1995

[51] Int. Cl.[6] .................................. C07C 2/56; C07C 2/58
[52] U.S. Cl. .......................... 585/722; 585/709; 585/717; 585/719; 585/730; 585/732
[58] Field of Search ...................... 585/730, 722, 585/719, 217, 732, 709

[56] References Cited

U.S. PATENT DOCUMENTS

| | | | |
|---|---|---|---|
| 3,644,565 | 2/1972 | Biale | 585/722 |
| 4,300,015 | 11/1981 | Kirsch et al. | 585/722 |
| 4,918,255 | 4/1990 | Chou et al. | 585/722 |
| 4,992,615 | 2/1991 | Huss, Jr. et al. | 585/722 |
| 4,992,616 | 2/1991 | Chou et al. | 585/722 |

OTHER PUBLICATIONS

CRC Handbook (CRC Press) 1976–1977, pp. C–146, C–217, C–229, C–449 and C–518.

*Primary Examiner*—Glenn A. Caldarola
*Assistant Examiner*—Elizabeth D. Wood
*Attorney, Agent, or Firm*—Watov & Kipnes

[57] ABSTRACT

Method of producing alkylates in which an isoparaffin, olefin, a diffusing agent and a solid, acid catalyst are combined to form a three phase reaction mixture; a hydrocarbon phase containing primarily isoparaffin, a diffusing agent phase containing the diffusing agent, olefin and diffuse isoparaffin and a solid, acid catalyst phase, the diffusing agent being a polar solvent in which the olefin and aromatics are soluble.

20 Claims, 1 Drawing Sheet

PROCESS OF PRODUCING ALKYLATES

TECHNICAL FIELD

The present invention relates to the catalytic alkylation of olefins with isoparaffins using a solid, acid catalyst.

BACKGROUND OF THE INVENTION

To create lighter hydrocarbons with greater commercial value, portions of crude oil are generally thermally or catalytically "cracked". Cracking produces light gaseous byproducts such as butylene, isobutane, propylene and propane. Other refining processes also produce some of these gaseous byproducts. These light gases are usually further processed to create larger hydrocarbon molecules of greater commercial value. One such process involves reacting isoparaffins with olefins to create "alkylates". For example, the alkylate produced by reacting an isoparaffin (e.g. an isobutane) with an olefin (e.g. isobutylene) consists primarily of 2-2-4 trimethylpentane, which is the molecule whose combustion defines an octane number of 100. Alkylates are generally highly branched hydrocarbons that have high octane numbers and desirable volatility characteristics. They are particularly useful as components of a reformulated gasoline ("RFG"). RFGs are required to meet the highly restrictive emission standards under the Clean Air Act.

Alkylates are commercially produced in oil refineries by reacting isoparaffins with olefins in the presence of anhydrous hydrofluoric acid or sulfuric acid, which acids serve as catalysts for the reaction. Boron trifluoride and other halides have been examined for use as catalysts to produce alkylate, but have not been commercially accepted. Hydrofluoric acid and sulfuric acid, however, have severe environmental shortcomings, which have led to ongoing efforts to find alternative processes for producing alkylates.

Solid catalysts have long been employed in the petroleum industry. They have, however, been ineffective in catalyzing the formation of isoparaffin alkylates because of the chemical inactivity of isoparaffins and because the solid catalysts rapidly accumulate "coke" deposits.

In other processes, such as the alkylation of benzene to produce ethyl benzene or cumene, the buildup of coke is relatively slow and solid catalysts such as ZSM-5 are satisfactory. This is because benzene and other aromatics are sufficiently reactive to be easily alkylated.

To the contrary, isoparaffins including isobutane are relatively inert or unreactive and have required special measures such as the use of strong acids to achieve alkylation. As indicated above, the use of strong acids such as hydrofluoric acid and sulfuric acid presents environmental problems.

It would therefore be a significant advance in the art of producing alkylates if the reaction of isoparaffins and olefins could be carried out using environmentally acceptable materials.

SUMMARY OF THE INVENTION

The present invention is directed to a method of producing alkylates from an isoparaffin and an olefin wherein the reaction is catalyzed with a solid, acid catalyst. More specifically, the present method comprises.

a) combining an isoparaffin and an olefin in a diffusing agent to form a reaction mixture, said diffusing agent comprising a polar solvent in which the olefin is soluble and in which the isoparaffin has at least limited solubility.

b) reacting the mixture produced in step (a) in the presence of a solid acid catalyst under conditions in which at least a portion of the isoparaffin reacts with at least a portion of the olefin to produce the alkylates.

BRIEF DESCRIPTION OF THE DRAWING

The following drawing is illustrative of an embodiment of the present invention and is not intended to limit the invention as encompassed by the claims forming part of the application.

DETAILED DESCRIPTION OF THE INVENTION

Figure 1:
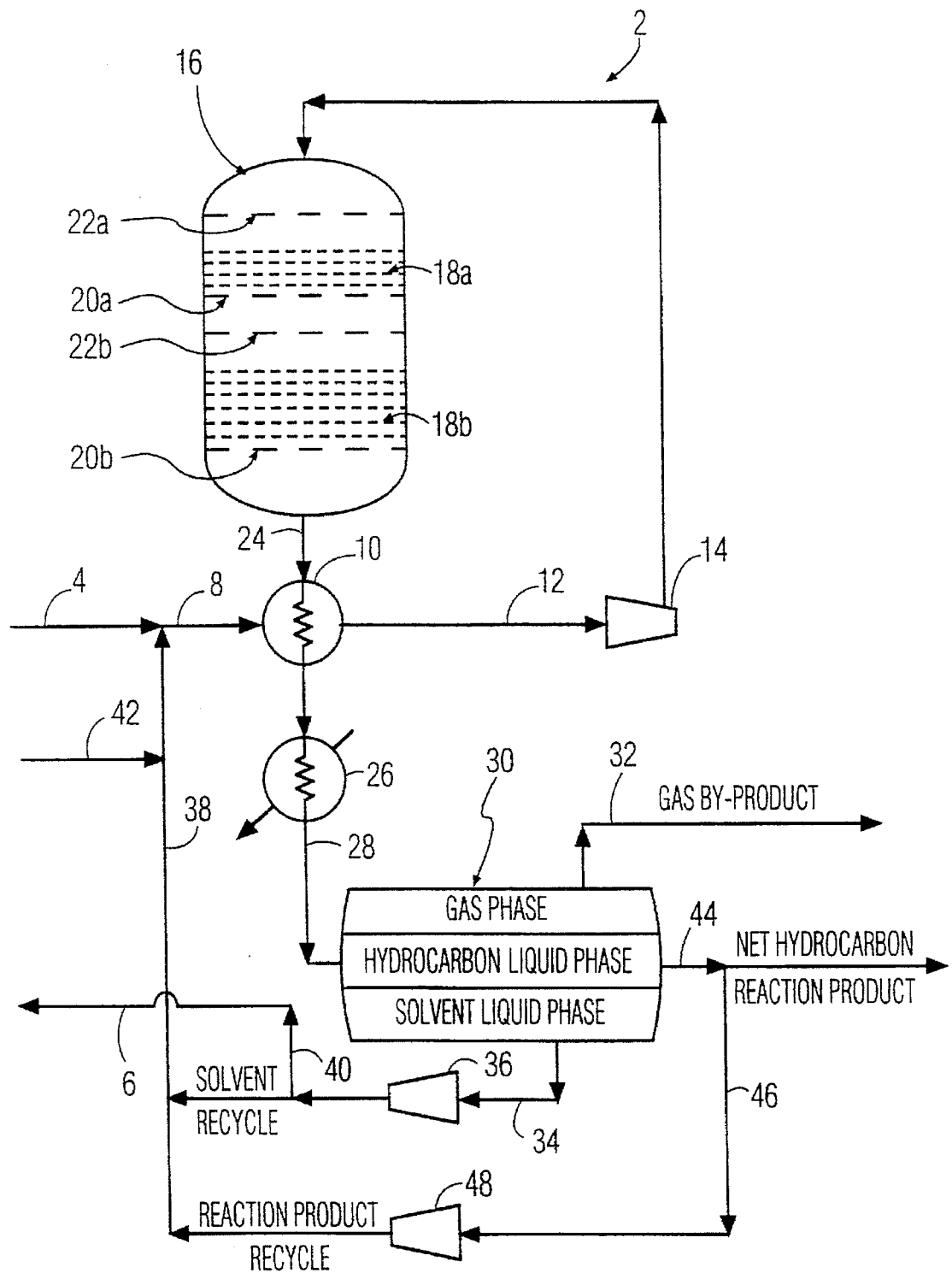
FIG. 1 is a schematic view of one embodiment of the present invention.

The process of the present invention will generally comprise three phases, a hydrocarbon phase comprised primarily of the isoparaffin, a diffusing agent phase comprised of the diffusing agent, olefin and diffuse isoparaffin, and solid catalyst phase. While not wishing to be limited by theory, it is believed that the diffusing agent more effectively wets the solid catalyst than does the hydrocarbon phase, such that catalytic alkylation primarily occurs at the interface of the diffusing agent and the solid catalyst phase. Also, under some operating conditions the hydrocarbon phase will be substantially gaseous, leaving only the diffusing agent phase to wet the catalyst. Any polymer that does form in the reaction is solubilized by the diffusing agent, thereby limiting the degree to which it poisons the solid catalyst. Also, the solubilization of the polymer will allow for the use of continuous processes wherein excess polymer can be removed from such processes by removing a portion of the diffusing agent and distilling it to separately recover purified diffusing agent and the polymer.

With regard to the principal materials for the process of the present invention, isoparaffins having 4 or 5 carbon atoms are preferred. Isobutane is the most preferred isoparaffin for the production of reformulated gasoline.

The preferred olefins are those having 3 to 5 carbon atoms. In particular, the preferred olefins include propylene, butylene and pentylene.

The isoparaffin is typically present in the reaction in an amount greater than the olefin, preferably in a molar ratio of at least about 4:1, most preferably at least about 8:1. Higher ratios of isoparaffin to olefin are preferred to suppress the tendency of the olefins to form undesirable polymerization byproducts.

The diffusing agents are employed to activate the isoparaffin in the process and the principal component thereof is a polar solvent. The amount of the polar solvent may vary over a wide range but is typically about a 1:1 volume ratio with the hydrocarbon feed. The polar solvents preferred for use in the present invention include those that selectively absorb olefins and aromatics, yet are substantially immiscible with paraffins and have an affinity for water. The solvent therefore enables the diffuse isoparaffin and the absorbed olefin to react in the solvent phase on contact with the catalyst.

The preferred polar solvents for use as the diffusing agent include liquid $SO_2$, liquid $CO_2$, phenol, cresol, Selexol (a proprietary aromatic extraction solvent marketed by Union Carbide), glycols, dimethylformamide, furfural, tetrahydrofuran, dioxane, mixtures thereof and the like.

The diffusing agent may also include acid oriented promoters such as HCl, $SO_3$ and $Cl_2$ to enhance diffusion of the isoparaffin in the polar solvent. The acid oriented promoters are typically present in an amount of from about 0 to 50 ppm based on the reaction mixture, preferably from about 0 to 25 ppm.

In accordance with the present invention it is preferred that the olefin is more soluble in the polar solvent than the isoparaffin. More specifically, the isoparaffin is generally soluble in the diffusing agent in an amount of at least about 5 g/L, preferably at least about 30 g/L. Preferably the upper limit of solubility of the isoparaffin in the polar solvent is about 200 g/L, most preferably 100 g/L.

The olefin is preferably soluble in the polar solvent in an amount of at least about 200 g/L, most preferably at least about 500 g/L.

The solid catalysts employed in the present invention have a strong acid function and include aluminosilicates, zeolites (e.g. ZSM-5 marketed by Mobil Oil Corporation and Amberlite-type zeolites marketed by Rohm and Haas Corporation), faujasite, mordenite, mixtures thereof and the like. The most preferred solid acid catalysts for use in the present invention are faujasites. The catalytic activity of the solid, acid catalysts can generally be enhanced by adding small amounts of a catalytic promoter such as the noble metals platinum and palladium.

The process of the present invention will now be described in more detail with reference to FIG. 1. The system of the present invention for catalytically reacting isoparaffins with olefins is shown generally by numeral 2. A feed of hydrocarbons (e.g. isobutane and butylene) obtained from a source (not shown) is forwarded via a conduit 4 to be combined with a diffusing agent made up principally of a polar solvent (e.g. liquid $SO_2$) and optionally a minor amount of one or more acid oriented promoters (e.g. HCl). The polar solvent includes restored and makeup solvent, and, as specifically shown in FIG. 1, recycled solvent and/or solvent contained with a reaction product recycled portion as described hereinafter.

The solvent for the system flows through the conduit 6 and combines with the hydrocarbon feed from the conduit 4. The combined stream flows via the conduit 8 to a heat exchanger 10 to obtain heating duty. The heated combined stream is sent via a conduit 12 to a pump 14 where the combined stream is emulsified prior to entry into the reactor 16.

The reactor 16 shown in FIG. 1 contains two catalyst beds 18a and 18b and corresponding supports 20a and 20b and distribution trays 22a and 22b whose function and operation is well known. The emulsified reaction mixture from the pump 14 flows into the top of the reactor 16 and the mixture is reacted therein and removed from the reactor 16 via the conduit 24 into the heat exchanger 10 to provide heat to the combined stream flowing therein as previously described.

The reaction mixture is cooled in a condenser and flows via a conduit 28 to a phase settler 30 where the reaction product is separated from the other constituents of the resulting reaction. More specifically, the reaction product mixture is separated into a gas phase containing gas byproducts which leaves the phase settler 30 via a conduit 32. A solvent phase leaves the phase settler 30 via a conduit 34 and a pump 36 where a portion is sent to a solvent line 38 for recombination with the hydrocarbon feed at conduit 4. Another portion of the solvent phase is sent via a conduit 40 to be restored (e.g. to raise the purity by removing contaminants) and then combined with new solvent. The combination of restored and new solvent is sent via a conduit 42 to combine with the solvent stream in conduit 38.

The desired alkylates and unreacted feed materials are removed as a liquid phase from the phase settler 30 via a conduit 44. A portion of the reaction product is transported via a conduit 46 and a pump 48 to the solvent line 38 for combining with the hydrocarbon feed in line 4.

While the process of the present invention will minimize coking of the catalyst, it will from time to time be necessary to regenerate the catalyst. For a number of mineral based catalysts, this can be accomplished, for example, by calcining the catalyst in the presence of oxygen at temperatures sufficient to combust the coke contaminant.

Typically an emulsion of feed stock that includes the reactants and the diffusing agent will be passed over a bed of catalyst as described specifically in FIG. 1. The material that exits the catalyst bed can be re-fed to the catalyst bed or diverted for separation into its component parts. In this way, concentration of the reactants that pass over the catalyst can be more closely controlled. Also, the time of contact between the alkylate product and the catalyst can be controlled.

The alkylation process is highly exothermic. Thus, the flow rate of diffusing agent over the catalyst bed can also be used to limit heat build up. Preferably, the diffusing agent will have a specific gravity that is higher than that of the reactants and products. Preferably, the reactor will be operated to avoid drying the surface of the catalyst. Drying of the catalyst will accelerate the build up of polymeric byproducts on the catalyst, leading to early deactivation of the catalyst.

As discussed above, many solid catalysts can be rejuvenated by calcination. However, there will be a limit to the number of times that the catalyst can be regenerated in this way. Eventually, the catalyst will be sufficiently damaged such as by loss of crystalline structure, or the accumulation of nondegradeable deposits that it will have to be replaced.

The process of the present invention can be conducted by contacting the reactants, diffusing agent and solid catalyst in a slurry of the various phases. However, the engineering challenges to managing such a system are significant. A preferable approach as shown specifically in FIG. 1 is to create an emulsion of reactants and diffusing agent and pass the emulsion over a fixed bed of a particle form of solid catalyst.

The process of the present invention as for example shown in FIG. 1 can be varied by those skilled in the art. For example, the pressure in the reactor can be varied over a range of pressures. However, the pressure should be sufficient to maintain the diffusion agent in the liquid phase. In addition, the activity of the catalyst system can be enhanced by adding minor amounts of one or more noble metals or other catalyst enhancing agents such as aluminum chloride. Further, the relative amounts of the reactants and additives can be adjusted according to need.

In conducting the present process, it is preferred that sufficient diffusing agent be present in the liquid phase to wet the catalyst bed. If the catalyst bed is permitted to dry, polymeric byproducts will not be effectively washed from the surface of the catalyst, resulting in more rapid catalyst deactivation.

The catalyst supports 20a and 20b described in FIG. 1 should be capable of retaining the catalyst while allowing the reaction mixture and resulting product to flow therethrough. In addition, the support should be inert to the reaction mixture. A preferred support meeting this criteria is perforated metal plates overlaid by wire cloth and covered with inert ceramic pellets.

As previously indicated, the molar ratio of isoparaffin to olefin in the feed stock is preferably at least about 4:1, most preferably at least about 8:1. Typically, the feed stock will contain small amounts of normal butane and propane. These components are inert and will not diminish reaction efficiency unless present in very high concentrations. Typical refinery feed stocks will also contain smaller amounts of diolefins, acetylenic compounds, mercaptans, dissolved water and suspended solids. The presence of some amount of these compounds is generally unavoidable. However, it is preferred, to the extent economically feasible, to avoid these compounds since they will contribute to the deactivation of the catalyst.

It is preferred to recycle at least a portion of the hydrocarbon product containing the desired alkylates. It is believed that the presence of some reaction product in the reaction materials fed to the reactor will further dilute the olefin feed and suppress polymerization. The recycle hydrocarbon may also contain an amount of unreacted olefin present from the initial pass through the catalyst bed. Such recycling also adds inert components which will moderate the temperature rise in the reactor due to the heat of reaction. The weight ratio of recycled hydrocarbon to hydrocarbon feed will preferably range from about 0 to about 10, more preferably from about 0 to about 2.

The operating pressure and temperature of the reaction will depend on the properties of the diffusing agent and the activity of the catalyst. Very high operating pressures will be needed to maintain certain of the lower boiling diffusing agents, such as liquid $CO_2$ in the liquid phase. While the operating temperature will also vary, particularly with the selection of the diffusing agent, temperatures between about 50° F. and about 400° F. are preferred. More preferred are temperatures between about 100° F. and about 250° F. One reason to operate the process within these temperature ranges is to increase the activity of the catalyst while avoiding conditions that tend to adversely affect the catalyst.

With some diffusing agents, the operating temperature will have to be kept low to avoid drying the catalyst bed. Thus, catalysts that are active at low temperature will sometimes be needed. Such low temperature activity can be enhanced by introducing a Friedel-Crafts promoter such as aluminum chloride into the catalyst. Typically, aluminum chloride can be applied to the catalyst by sublimation. Typically, about one g of ammonium chloride is added per 1000 g of catalyst, preferably one g per 100 g of catalyst. The promoter is typically reapplied to the catalyst after each regeneration cycle.

Preferred diffusing agents should be compatible with operating temperatures of about 300° F. or higher. At such high temperatures, a substantial portion of the hydrocarbon feed will be in the vapor phase, while the diffusing agent should remain in the liquid phase. Phenol (melting point 106° F., boiling point 360° F.) and mixed cresols having a melting point of about 90° F. and a boiling point of about 390° F. are preferred solvents. Glycols, furfural and Selexol™ are also preferred diffusing agents. The hourly space velocity of the process of the present invention is preferably between about 0.1 and about 2.0 L of the liquid equivalent of the olefin feed per L of catalyst volume. More preferably, the hourly spaced velocity is about one L per L.

When high temperatures or high pressures are needed to operate the process of the invention, vessels adapted for high temperature and pressure will be employed as understood by those skilled in the art.

EXAMPLE 1

The process of the present invention is operated using the apparatus of FIG. 1.

A hydrocarbon feed containing 80% by weight isobutane, 10% by weight of mixed butylenes and 5% by weight of each of propane and n-butane is combined with phenol in a 1:1 volume ratio and 10 ppm of $SO_3$ based on the reaction mixture. The reaction mixture is passed through a dual bed catalytic reactor containing faujasite (zeolite X) as the catalyst at a space velocity of 1.0 L olefin/L catalyst. The initial reactor temperature is 125° F. and the temperature of the reactor at the end of the process cycle is 250° F. The pressure of the reactor is maintained at 400 psi.

The amount of hydrocarbon reaction product recycled through the conduit 46 and pump 48 is maintained in a 1:1 volume ratio with the amount of new hydrocarbon feed entering the system via the conduit 4. The amount of diffusing agent recycled through the conduit 6 is maintained at a 1:1 volume ratio with the combined amount of the hydrocarbon feed through the conduit 4 and the product recycle through the conduit 46 and pump 48.

By conducting the process in this manner, an alkylate product having an octane rating of about 93, an alkylate gravity of about 72 API and a yield of about 172 vol. % of the olefin contained in the hydrocarbon feed is obtained. The amount of alkylate produced is from about 20 to 200 barrels per pound of catalyst and from about 5 to 10 barrels per pound of diffusing agent.

While the embodiments set forth herein describe preferred features of the invention modifications may be made which are within the skill of those practicing in this art.

I claim:

1. A method of producing alkylates comprising:
    a) combining an isoparaffin and an olefin and a diffusing agent to form a reaction mixture having at least three phases, a hydrocarbon phase comprised primarily of the isoparaffin, a diffusing agent phase comprised of the diffusing agent, olefin and diffuse isoparaffin and a solid, acid catalyst phase, said diffusing agent comprising a polar solvent in which the olefin is soluble and in which the isoparaffin is soluble to the extent of from about 5 to 200 g/L; and
    b) reacting the mixture produced in step (a) in the presence of the solid, acid catalyst phase under conditions in which at least a portion of the isoparaffin reacts with at least a portion of the olefin to produce the alkylates.

2. The method of claim 1 wherein the isoparaffin has 4 or 5 carbon atoms.

3. The method of claim 2 wherein the isoparaffin is isobutane.

4. The method of claim 1 wherein the olefin has 3 to 5 carbon atoms.

5. The method of claim 4 wherein the olefin is selected from the group consisting of propylene, mixed butylenes and mixed pentylenes.

6. The method of claim 1 wherein the isoparaffin and olefin are present in a molar ratio of at least about 4:1.

7. The method of claim 6 wherein the isoparaffin and olefin are present in a molar ratio of at least about 8:1.

8. The method of claim 1 wherein the diffusing agent further comprises an acid oriented promoter.

9. The method of claim 1 wherein the solid acid catalyst is selected from the group consisting of aluminosilicates, zeolites, faujasites, mordenites and mixtures thereof.

10. The method of claim 1 wherein the solid acid catalyst further comprises a catalytic promoter.

11. The method of claim 10 wherein the catalytic promoter is a noble metal.

12. The method of claim 1 wherein the olefin is soluble in the diffusing agent in an amount of at least 200 g/L.

13. The method of claim 1 comprising conducting the reaction at a temperature of from about 50° to 400° F.

14. The method of claim 1 further comprising reacting the mixture in step (a) to produce a reaction product containing a byproduct containing gas phase, an alkylate containing liquid phase and a polar solvent containing liquid phase, and recycling a portion of the alkylate containing liquid phase to the reaction mixture.

15. The method of claim 14 wherein the weight ratio of the recycled portion of the alkylate containing liquid phase to the amount of the isoparaffin and olefin in the reaction mixture is up to 10:1.

16. The method of claim 1 wherein the combined amount of the isoparaffin and olefin to the amount of the diffusing agent is about 1:1 based on volume.

17. The method of claim 14 further comprising recycling at least a portion of the diffusing agent to the reaction mixture.

18. The method of claim 17 wherein at least a portion of the recycled portion of the diffusing agent is treated to raise the purity thereof.

19. The method of claim 1 comprising conducting the reaction at an hourly space velocity of from about 0.1 to 2.0 L of the liquid equivalent of the olefin per L of the catalyst volume.

20. The method of claim 9 wherein the solid acid catalyst is a mixture of aluminosilicates and zeolites.

* * * * *